Figure 1:
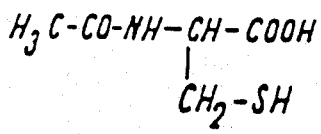
Figure 1:
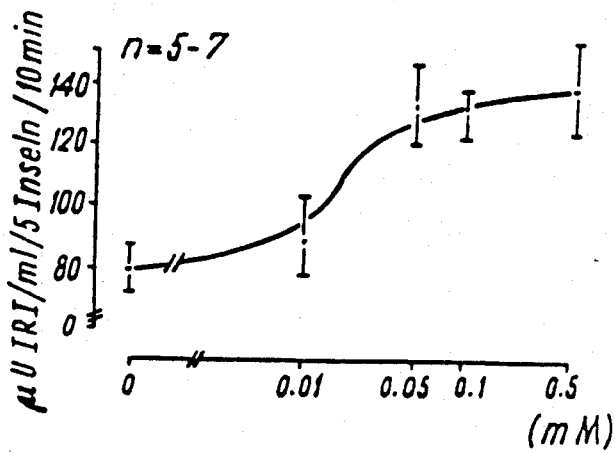

United States Patent [19]

Ammon

[11] Patent Number: 4,829,087
[45] Date of Patent: May 9, 1989

[54] UTILIZATION OF CYSTEINE DERIVATIVES OR SALTS THEREOF TO ENHANCE INSULIN SECRETION OF THE ISLETS OF LANGERHANS OF THE PANCREAS

[76] Inventor: Hermann P. T. Ammon, Im Kleeacker 30, D-7400 Tuebinger, Fed. Rep. of Germany

[21] Appl. No.: 762,194
[22] PCT Filed: Nov. 27, 1984
[86] PCT No.: PCT/EP84/00371
  § 371 Date: Jul. 26, 1985
  § 102(e) Date: Jul. 26, 1985
[87] PCT Pub. No.: WO85/02340
  PCT Pub. Date: Jun. 6, 1985

[30] Foreign Application Priority Data

Nov. 29, 1983 [DE] Fed. Rep. of Germany ....... 3343141

[51] Int. Cl.$^4$ .................... A61K 31/195; A61K 31/22
[52] U.S. Cl. .................... 514/562; 514/550; 514/866
[58] Field of Search .................... 514/3, 4, 665, 562; 515/550

[56] References Cited

PUBLICATIONS

*Chemical Abstracts*, vol. 71 (1969) 111089w.
*Chemical Abstracts*, vol. 99, (1983) 206966x.
*Chemical Abstracts*, vol. 96 (1982) 46096w.
Hermann P. T. Ammon, Andreas Grimm, Suszanne Lutz, Doris Wagner-Teschner, Monika Handel, and Ingrid Hagenloh, Diabetes, vol. 29, pp. 830-834, Oct. 1980.
H. P. T. Ammon, M. S. Akhtar, A. Grimm, and N. Niklas, *Naunyn-Schmiedeberg's Arch. Pharmacol.*, vol. 307, 91-96, 1979.
Hermann P. T. Ammon, Rolf, Hagele, Nabil Youssif, Roslindis Eujen, and Najiba El-Amri, *Endocrinology*, vol. 112, 720-726, 1983.
H. P. T. Ammon and M. Abdel-hamid, *Naunyn-Schmiedeberg's Arch. Pharmacol.*, vol. 317, 262-267, 1981.

*Primary Examiner*—Frederick E. Waddell

[57] ABSTRACT

Utilization of cysteine derivatives or the salts thereof having the formula:

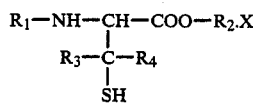

wherein $R_1$ is a hydrogen atom or an acetyl radical, $R_2$ is a hydrogen atom, a methyl radical or an ethyl radical, $R_3$ is a hydrogen atom or a methyl radical, $R_4$ is a hydrogen atom or a methyl radical and X is a Proton acid, to enhance the glucose-induced insulin secretion of the Islets of Langerhans of the pancreas.

1 Claim, 7 Drawing Sheets

N-Acetyl-L-cystein
$ED_{50} \sim 0{,}02$

L-Cystein-methylester-HCl
$ED_{50} \sim 0{,}4$

L-Cystein-aethylester-HCl
$ED_{50} \sim 0{,}5$

Homocystein

Dimercaptobernsteinsäure

2-Mercaptopropionylglycin
(Thiola)

2-Mercaptoethansulfonat-Na
(Mesna)

UTILIZATION OF CYSTEINE DERIVATIVES OR SALTS THEREOF TO ENHANCE INSULIN SECRETION OF THE ISLETS OF LANGERHANS OF THE PANCREAS

Diabetes (sugar sickness) can appear in different forms. The so called youth diabetes (Diabetes I) is characterized by the inability of the Islets of Langerhans of the Pancreas adequately to produce and deliver sufficient insulin for the elimination of glucose from the blood, which would be their function. Insulin has to be injected. Such patients are "insulin dependent." It is different with the so called old-diabetes (Diabetes II): which is characterized by the inability of the insulin which is present in the cells of the Islets of Langerhans to be delivered to the blood. Such patients are thus not "insulin dependent." Their treatment consists of special diet and, further, of substances which activate insulin secretion. Well-known substances for this are for example the sulphonyl ureas. They activate the secretion of insulin with a special process directly and/or together with an increase in blood sugar.

It is well known that there is a connection between the thiol content of the cells in the Islets of Langerhans and glucose-induced insulin secretion. Thereby it was revealed that the tripeptide glutathion, which is naturally contained in the Islets of Langerhans, forms a Redox-system and that a correlation exists between the relationship of reduced glutathion (GSH) to oxidized glutathion (GSSG) and the concentration of glucose during the induced secretion of insulin (Ammon et al., Diabetes 29 (1980), No. 10 P. 830-834). Furthermore the Redox-pair NADP/NADPH (Nicotinamide-adenine-dinucleotide-phosphate) serves as a hydrogen conveyor.

Furthermore, it is well known that chemical agents, which oxidize NADPH and GSH, inhibit glucose-induced insulin secretion (Ammon et al., Arch. Pharmakol. 207 (1979), P. 91-96; Ammon et al., Endocrinology, Vol. 112, No. 2 (1983), 720-726).

On the other hand, an addition of GSH and Cysteine "in vitro" revealed an increase in glucose-induced insulin secretion (Ammon et al., Arch Pharmakol. 317 (1981), P. 262-267). Further research has indicated that, despite the addition of GSH and Cysteine "in vitro," without a high enough concentration of glucose to effect stimulation, no insulin secretion will be caused. From all these observations, the stylized model pictured below was postulated, which shows the effect of the already mentioned Redox-pair. It is apparent from this that the permeability of the $\beta$-cell of an Islet of Langerhans, in the sense of greater or lesser insulin secretion, depends on the Redox condition of the SH-group membrane.

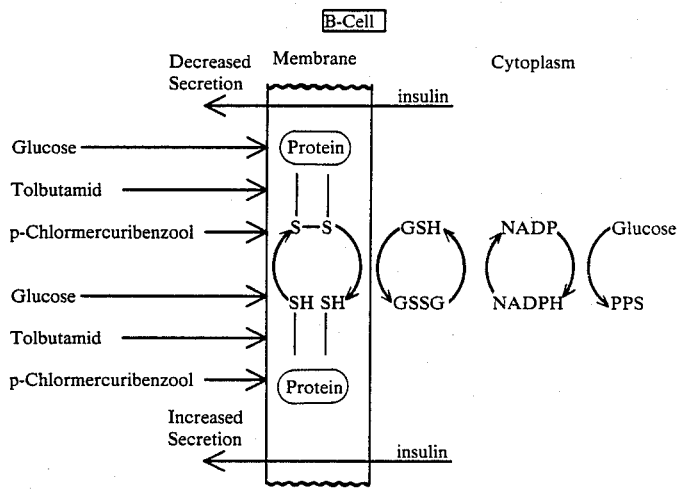

The protein of the membrane allows an increased secretion of insulin in a reduced state of the SH-groups, while in an oxidized state, only limited secretion is possible. This reduction of the Membrane-S-S-Groups through hydrogen transfer can occur through GSH formed from oxidized GSSG, which itself can once again be transferred into GSH, through the Redox-pair NADP/NADPH by means of hydrogen transfer. The NADP, formed thus by hydrogen transfer can, on the other hand, be transferred into the reduced form NADPH by hydrogen transfer out of the Glucose-PPS-(Pentosephosphateshunt) Path.

The inducement of increasing insulin secretion follows in this way:

Glucose—PPS-Path—NADPH—GSH
—reduced-Membrane-S—H—Groups.

Glucose increases the reduced glutathion concentration of the Islets of Langerhans and also the secretion of insulin, while the external addition of insulin leads to a decrease of the intracellular SH-content and to the inhibition of insulin secretion. The external supply of GSH magnifies the insulin liberating effect of glucose, whereas GSH in the absence of glucose has no effect.

The task of the discovery at hand is to show substances which will induce insulin secretion in the presence of glucose. Taking the above mentioned working model as a basis, the substances are those that increase the reduced thiol-group content of the $\beta$-cell and thereby take over the function of GSH, in that they push the Redox-condition of the membrane-like SH-groups of the $\beta$-cell toward the reduced side.

This objective is achieved by cysteine derivatives or the salts thereof, of the formula:

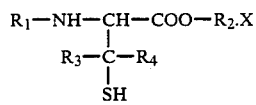

Further it is achieved with cysteamine of formula NH₂—CH₂—CH₂—SH. When these substances are added "in vitro" there is an increase in insulin secretion when the glucose concentration is increased beyond a certain threshold amount. As a measurement for the effectiveness, the commonly used pharmacological term of the so called "median effective dosage" $ED_{50}$, can be used in a slightly amended form. $ED_{50}$ is that amount of added thiol, measured in mM per ml of reaction solution, which is necessary to achieve 50% of the maximum achievable gain of insulin. The $ED_{50}$-value is also a measurement for the requisite dosage.

Resulting therefrom, one $ED_{50}$-value of the reduced form of glutathion (GSH) is 0.01. From the substances according to the discovery, it is indicated that cysteamine with an $ED_{50}$-value of 0.01 and N-acetyl-L-cysteine (NAC) with an $ED_{50}$-value of 0.02 have the best effects. Thus these substances are especially advantageous. Specifically, the $ED_{50}$-values for the individual substances are presented in the following table:

TABLE

| Thiol | ~$ED_{50}$-Value |
| --- | --- |
| Glutathion (GSH) | 0.01 |
| Cysteamine NH₂—CH₂—CH₂—SH | 0.01 |
| N—acetyl-cysteine (NAC) | 0.02 |
| CH₃—CO—NH—CH(CH₂SH)—COOH | |
| D-penicillamine | 0.2 |
| NH₂—CH(COOH)—C(CH₃)₂—SH | |
| L-cysteine-methyl ester.HCL | 0.4 |
| NH₂—CH(COOCH₃.HCL)—CH₂—SH | |
| L-cysteine-ethyl ester.HCL | 0.5 |
| NH₂—CH(COOC₂H₅.HCL)—CH₂—SH | |
| N—acetyl-D-penicillamine | 1.0 |
| CH₃—CO—NH—CH(COOH)—C(CH₃)(CH₂)—SH | |

In the case of N-acetyl-L-cysteine and other cysteine derivatives, there is a fundamentally different working mechanism from the well known sulphonyl ureas. Already therein lies an advantage, as one also endeavours to cure certain illnesses through pharmacology with different working mechanisms. This makes it possible to switch to a different course, when a particular course cannot be followed for certain reasons. Another important advantage is that N-acetyl-L-cysteine and other cysteine derivatives have no separate effect on insulin secretion, but only produce an effect, when the glucose concentration has exceeded a certain threshold amount. It functions, therefore, as an "intensifier" at the appearance of the conditions which normally induce the secretion of insulin (the presence of glucose). Thus it should not be feared that glucose will also be eliminated from the blood by increased insulin secretion, if the glucose concentration has not yet exceeded its normal amount. This means that no hypoglycemic side effects need be feared.

In addition N-acetyl-L-cysteine and cysteine derivatives respectively intensify the effect of the well known sulphonyl urea, Tolbutamide. Both substances magnify each other. N-Acetyl-L-cysteine consists of two physiological foundation blocks which can be easily metabolized. It is therefore a substance from which undesirable side effects should hardly be feared.

In each case, application can ensure before food intake; the effect will only commence upon consumption of food, i.e. with the increase of glucose concentration in the blood, and will cease when glucose has returned to its normal amount. Further, it emerges that one can get by with reasonable amounts with regard to dosage. The ability to have an effect remains unchanged in the body over a certain period; within this period, lasting at least 30–60 minutes, food intake may proceed, the consequence of which is an increase in glucose concentration, which is then reduced by the boosted insulin secretion, as stimulated by the N-acetyl-cysteine.

In view of these special characteristics, N-acetyl-L-cysteine was tested "in vivo." This justifies the deduction that, as with the other substances, those qualities found "in vitro" would also appear "in vivo." The substances in this category are generally composed of materials which are known not be be species-specific, thus fundamentally the effect, shown in the following experiments, is also to be assumed in humans.

The discovery is not being suggested in that N-acetyl-L-cysteine is already known for another indication. Until now, it has been used as an expectorant for Mucoviscidosis, and as a liver protector. From this indication it cannot be deduced that it can also be used for the purpose described here, namely the stimulation of insulin secretion of the Islets of Langerhans of the pancreas for the treatment of Diabetes II.

The discovery can also be realized, when the SH-group is supplied with an intracellularly detachable protective group.

Figure 11:
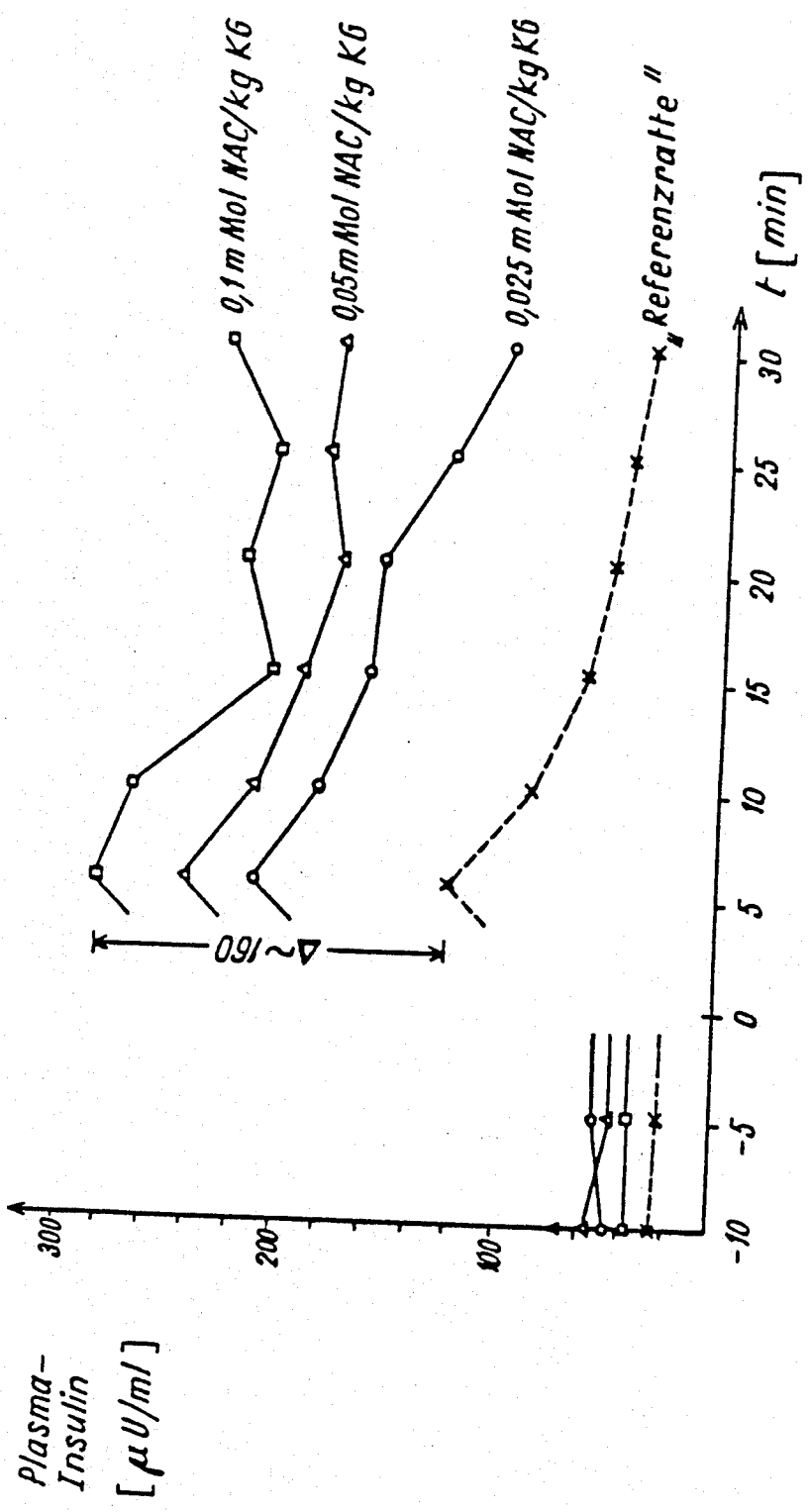
Figure 12:
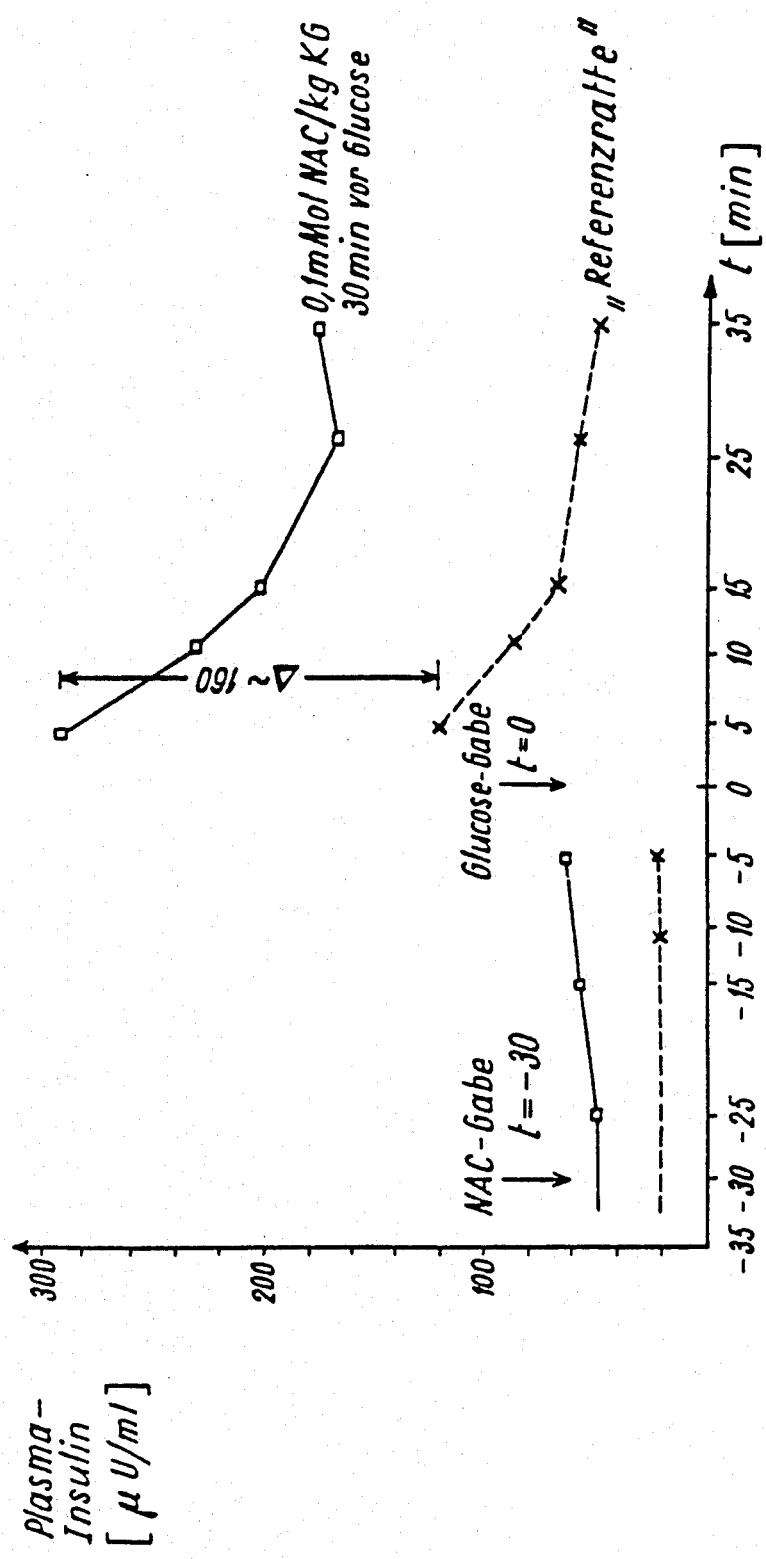
Figure 13:
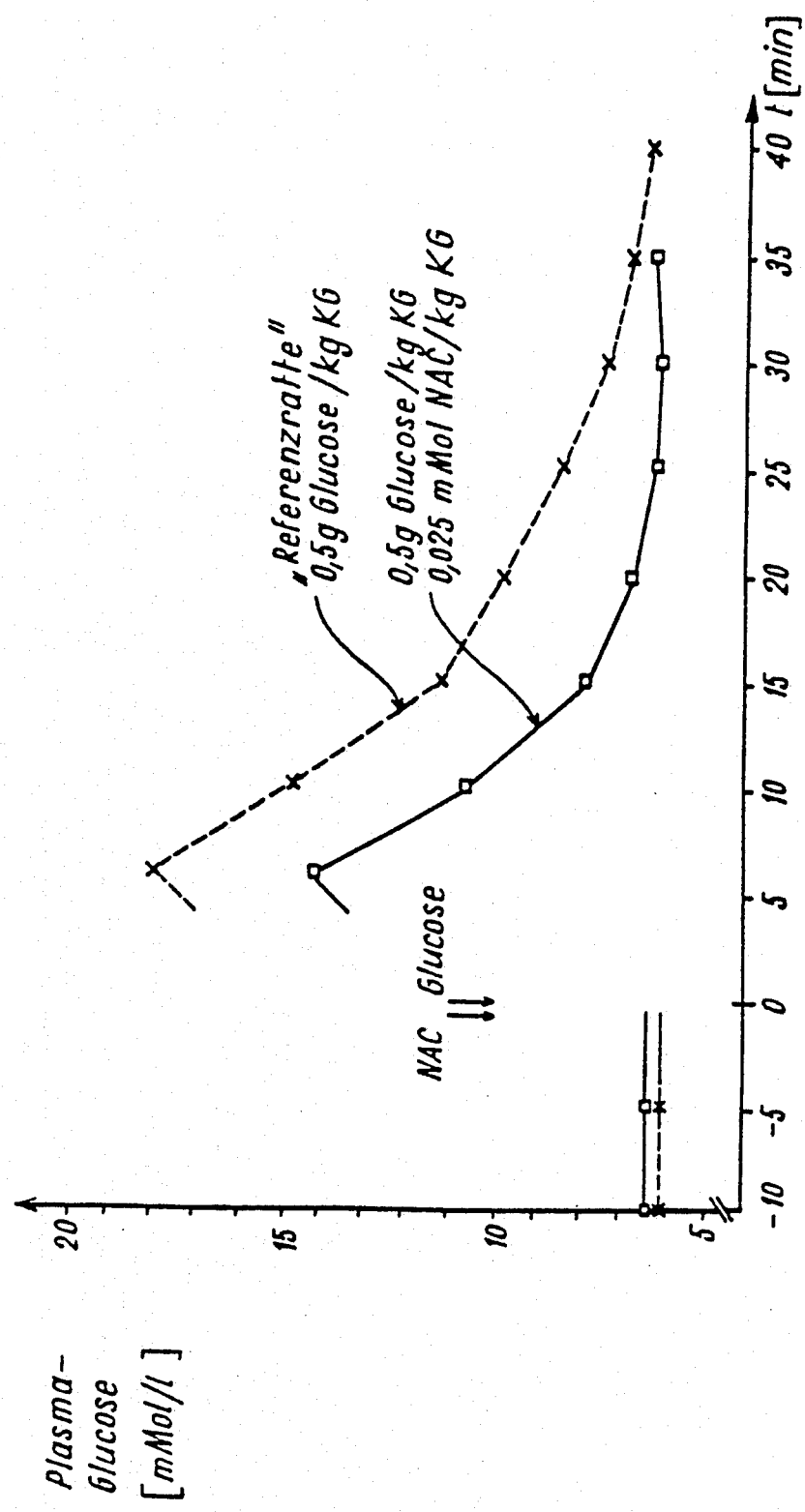

The following are some examples of the execution of the discovery, described in greater detail. Shown in:

FIG. 1–10: the effect "in vitro" of various different thiols on glucose-induced insulin secretion of the Islets of Langerhans;

FIG. 11: the effect "in vivo" of N-acetyl-L-cysteines on glucose-induced insulin secretion;

FIG. 12: the effect of N-acetyl-L-cysteines when injected before the glucose;

FIG. 13: the chronological development of the glucose concentration in rat plasma, measured in mM/l, through the injection of N-acetyl-L-cysteine.

In all diagrams, the statistical averages of the experiments, which have been carried out several times (n), are shown. The so called "Student's T-test" was used to arrive at the statistical valuation. In order to effect comparative studies of the individual measurement results, the "median effective dosage" $ED_{50}$ was determined, i.e. that dosage which produces 50% of the maximum therapeutic effect. That is the exact amount of thiol, which is necessary to achieve 50% of the maximum secretion of insulin.

Figure 2:
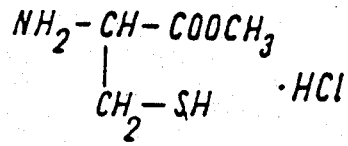
Figure 2:
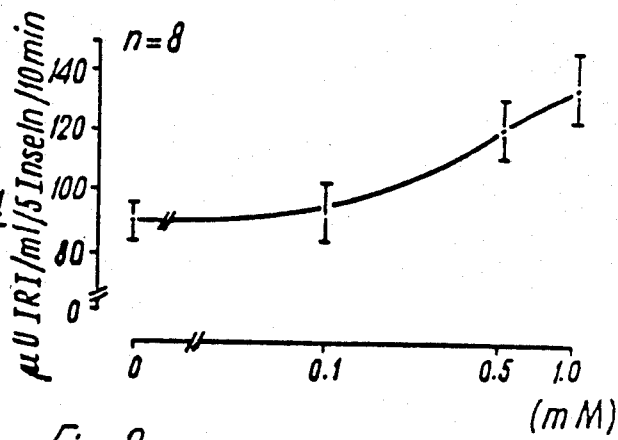
Figure 3:
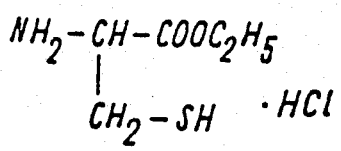
Figure 3:
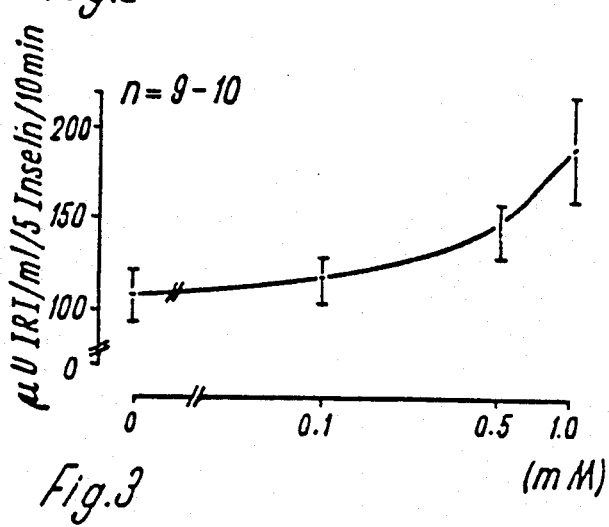

The experiment examples shown in FIGS. 1–3 indicate that N-acetyl-cysteine (NAC) with an $ED_{50}$-value of approximately 0.02 compared with Ester-Hydrochloride (Methyl ester 0.4, Ethyl ester 0.5) has the best effect as regards the increase in induced insulin secretion.

Animals from both sexes were taken from local stock. They weighed approximately 300 g and were fed a standard diet (Altromin). The Islets of Langerhans were isolated according to Lasy and Kostianovsky (Diabetes 16 (1967), P. 35–39). The insulin determination followed pursuant to Söldner and Slone (Diabetes 14 (1965) P. 771–779). As a result, glucose and thiol were administered almost immediately. As an ordinate, the insulin content per ml of experimental solution per 5 Islets of Langerhans, was applied after 10 minutes. "Micro Units of Immunoreactive Insulin" (1UIRI) serve as the unit of the depicted graphs. On the opposite axis, the addition of thiol in mM per volumes of experimental solution, is shown.

FIGS. 1–3 show the effect of N-acetyl-L-cysteine (NAC), L-cysteine methyl ester.HCL as well as L-cysteine ethyl ester.HCL on the insulin secretion of the Islets of Langerhans of rats induced by 11.1 mM of glucose.

Figure 4:
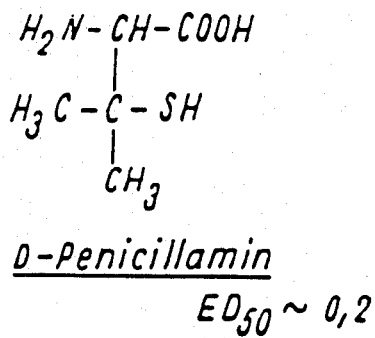
Figure 4:
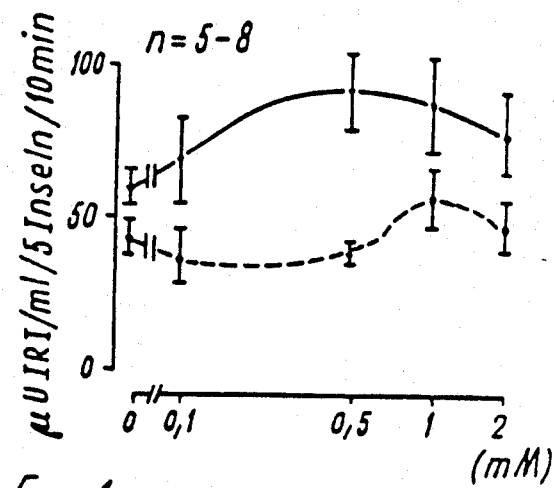
Figure 5:
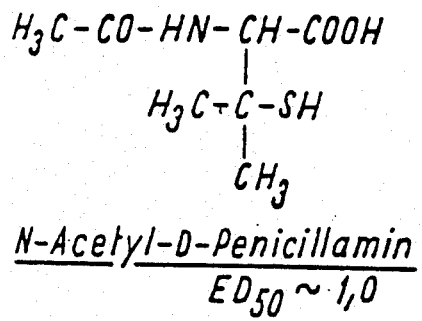
Figure 5:
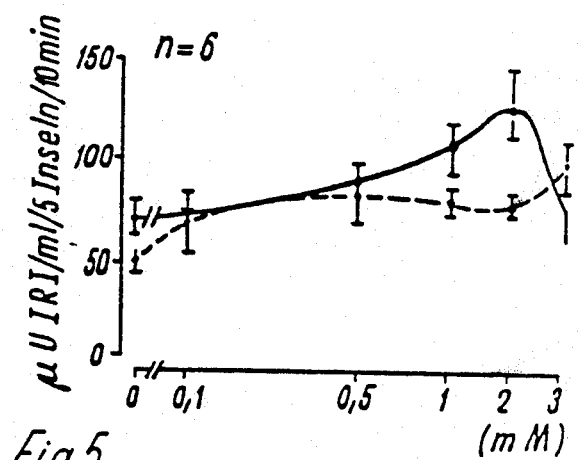
Figure 6:
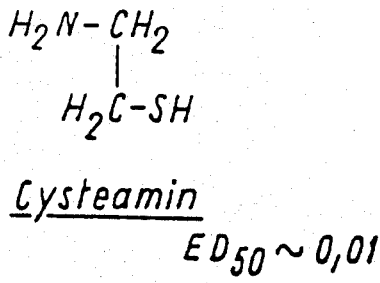
Figure 6:
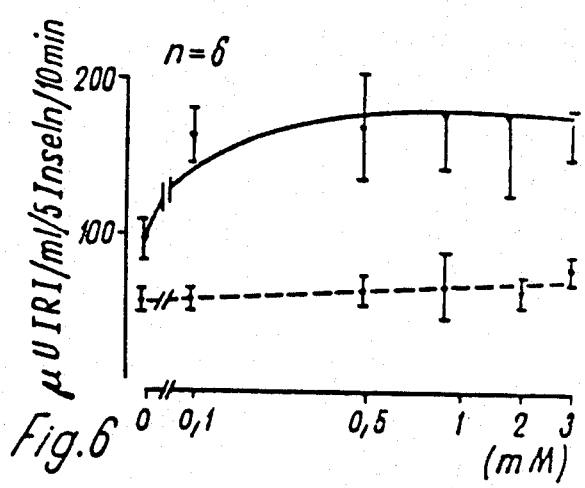
Figure 7:
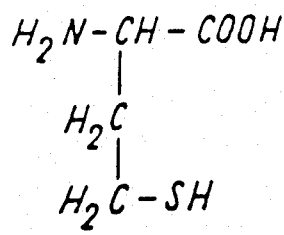
Figure 7:
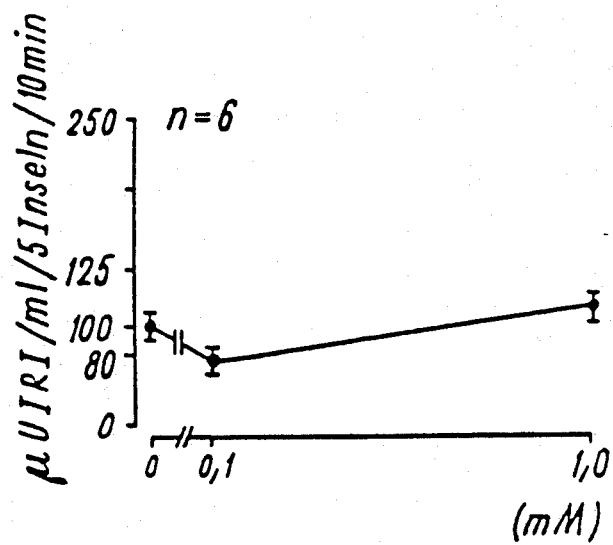
Figure 8:
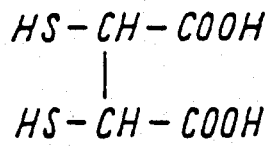
Figure 8:
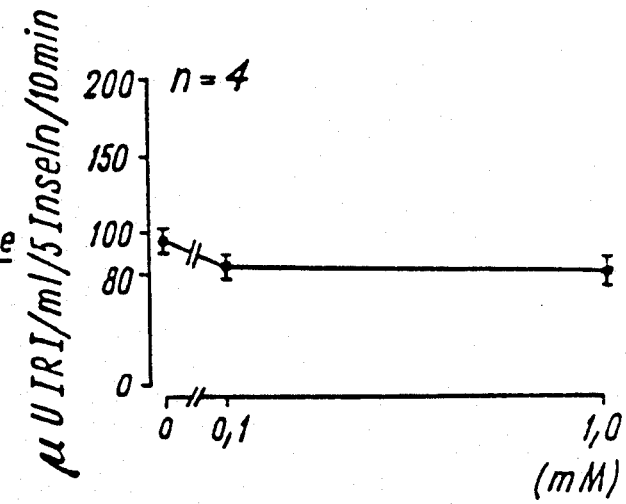
Figure 9:
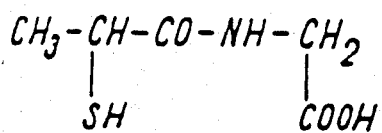
Figure 9:
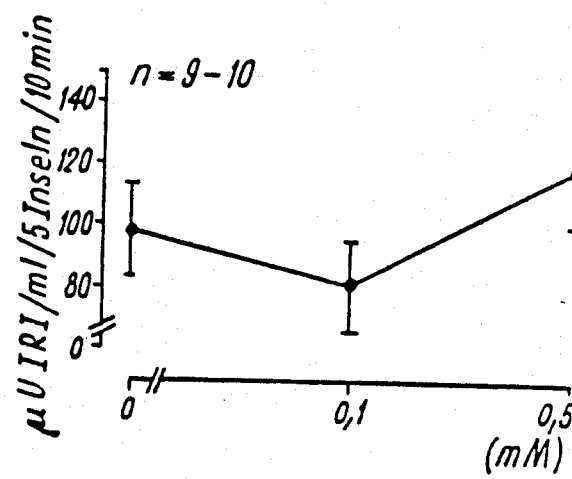

FIGS. 4 and 5 show the experiment results of two more cysteine derivatives, namely D-Penicillamine and N-acetyl-D-penicillamine, just as in FIG. 6 cysteamine. In these diagrams, the dotted lines show the results with a glucose concentration of 2.8 mM, which on its own does not induce insulin secretion; the fully drawn lines indicate the results with a glucose concentration of 11.1 mM. The $ED_{50}$-value for the D-penicillamine was 0.2, for the N-acetyl-D-penicillamine was 1.0, and for the cysteamine was the noticeable amount of 0.01.

An interpretation of the experiment results with the minimal glucose concentration (2.8 mM for the dotted line) can be made to the effect that, under a certain threshold concentration of glucose, when cysteine derivatives, the salts thereof, or cysteamine are added, there is no resultant increase in insulin secretion. This means, especially when translated into later pharmacological applications, that induced insulin secretion results only after a certain blood sugar concentration has been exceeded as, for example, after food intake.

FIGS. 7 through 10 show, for delineation, the experiment results of cysteine-like substances which also contain thiol-groups. Homocysteine (cf. FIG. 7) is differentiated from cysteine only because of the addition of a $CH_2$-group; it is thus closely related to cysteine, but certainly no derivative. With this there is no effect on the glucose-induced insulin secretion.

Figure 10:
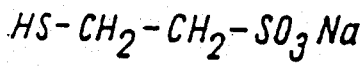
Figure 10:
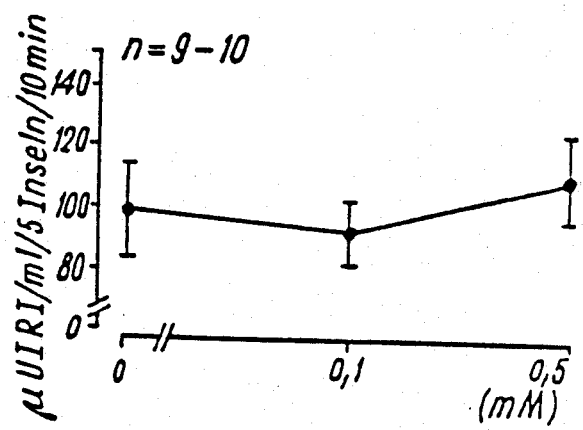

FIG. 10 shows the effect of 2-Mercaptoethansulfonate sodium salt (Mesna) which contains both a thiol-group and a sulfo-group, so that, for this reason, the effect of stimulation of insulin secretion could be assumed. However, such an effect was not observed.

FIG. 11 shows the experiment results for "in vivo" experiments using N-acetyl-L-cysteine ($ED_{50}$ 0.02) in rats. Here, the insulin content of the plasma is measured in "Micro Units per ml" ($\mu$U/ml) against the time applied. The dotted line shows the change of plasma insulin of rats who, at time t=0, were administered with 0.5 g of glucose per Kg of body weight; this dotted line is the reference curve; it shows the "normal" characteristics of rats without additional administration of thiols.

In FIG. 11, the fully drawn lines which show the change of plasma insulin in rats, who at time t=0 were administered with a 0.05 g dosage of glucose per Kg body weight (g/kg KG), and 0.5 minutes (t=−0.5) before this time were administered with an additional 0.1 or 0.05 or 0.025 mM of NAC/kg KG. In time increments of 5 minutes (t=5, 10, 15, 20, 25, 30 Min) the plasma insulin of the animals was ascertained. The curve indicates unequivocally the insulin secretion increased by NAC.

In FIG. 12 those experiments are shown, wherein the reaction conditions were changed from those shown earlier, in that the NAC was administered before the glucose. The glucose of dosage 0.1 mM/kg KG was given at time t=0. However, the NAC was administered 30 minutes before the glucose (t=−30 Min). It is clear that the NAC alone has no stimulating effect on the insulin secretion, instead that the inducement mechanism begins only with the addition of glucose. From this curve there is a further particularly advantageous effect to be gathered from the herein described discovery; namely, if one compares the plasma insulin content of the rats who were given N-acetyl-cysteine with those rats who were given no injection, both at time t=5, with those in FIG. 11, at the same time, who were administered with 0.1 mM NAC/kg KG, it can be determined that there is no difference ($\approx$160 $\mu$U). This also means that NAC, after it has already been in the rats' bodies for 30 minutes, has the same effect regarding the positive increase in insulin secretion as in FIG. 11, which shows the effect of NAC with an almost simultaneous (30 second difference) addition of glucose. It follows: that N-acetyl-L-cysteine is not eliminated in the space of at least 60 minutes to the degree that its effects as described above are no longer present. Translated into a possible therapeutic framework, this means that the application of a medication with an active ingredient of N-acetyl-L-cysteine to combat Diabetes II can be made in all cases before food intake, and its pharmacological effect will be retained until the increase in blood sugar, which results therefrom.

FIG. 13 shows the chronological progression of the change in concentration of plasma glucose (mM per liter). There, the dotted line shows the values for the "reference rats," (no addition of N-acetyl-L-cysteine) who at time t=0 were administered with a dose of 0.05 g glucose/kg KG. The fully drawn line shows the change in the "N-acetyl-L-cysteine rats" (administered with NAC) who at time t=−0.5 were administered with an additional 0.025 mM NAC/kg KG. With the "NAC-rats" the plasma glucose is already noticeably less than that of the "reference rats" at time t=5 because of the increased insulin output. The glucose amount recedes noticeably faster to the "normal amount." However it does not fall under this amount. This once again means, when translated into a possible therapeutic framework, that the blood sugar content will not rise too much with food intake, only to fall rapidly to its "normal amount." Thereby it will not fall under the "normal amount" (no "sugar deficiency").

Thereby, the effect postulated at the outset, namely the direct effect of glucose and thiol in the reaction process, has further support. In contrast, the medicines used until now to fight Diabetes II show hypoglycemic effects. Thus it is possible, especially through inattention to consideration of age by unprescribed dosages, especially by excessive dosage, to approach life threatening situations for the patient. Now, after this discovery, there is a medicine available for a wide field of utilization without these dangers.

I claim:

1. A method for enhancing the glucose-induced insulin secretion of the Islets of Langerhans of the pancreas in a person in need of insulin secretion enhancement, which method comprises administration of N-acetyl cysteine to said person in an amount sufficient to enhance the glucose-induced insulin secretion of the Islets of Langerhans.

* * * * *